United States Patent
Sano et al.

(10) Patent No.: US 7,158,895 B2
(45) Date of Patent: Jan. 2, 2007

(54) DEVICE FOR DETECTING HYDROGEN CONCENTRATION AND METHOD OF DETECTING HYDROGEN CONCENTRATION

(75) Inventors: Yukihiro Sano, Takahama (JP); Yukihiro Takeuchi, Nishikamo-gun (JP); Yositugu Abe, Anjo (JP)

(73) Assignee: Denso Corporation, Kariya (JP)

( * ) Notice: Subject to any disclaimer, the term of this patent is extended or adjusted under 35 U.S.C. 154(b) by 18 days.

(21) Appl. No.: 11/055,382

(22) Filed: Feb. 10, 2005

(65) Prior Publication Data

US 2005/0182574 A1   Aug. 18, 2005

(30) Foreign Application Priority Data

Feb. 12, 2004 (JP) ............... 2004-035242

(51) Int. Cl.
G01N 27/18 (2006.01)
(52) U.S. Cl. ............ 702/30; 73/23.21; 204/424; 204/426
(58) Field of Classification Search ............ None
See application file for complete search history.

(56) References Cited

U.S. PATENT DOCUMENTS

| | | | | |
|---|---|---|---|---|
| 5,567,877 A | * | 10/1996 | Nishio et al. | 73/504.06 |
| 5,897,766 A | * | 4/1999 | Kawatsu | 204/426 |
| 5,945,601 A | * | 8/1999 | Hosoi et al. | 73/514.33 |
| 6,533,911 B1 | * | 3/2003 | Fujita et al. | 204/424 |
| 6,840,086 B1 | * | 1/2005 | McCoy et al. | 73/40.7 |
| 6,923,053 B1 | * | 8/2005 | Yamada et al. | 73/204.26 |
| 2003/0183000 A1 | * | 10/2003 | Yamada et al. | 73/204.26 |
| 2004/0016283 A1 | * | 1/2004 | Wang et al. | 73/1.02 |
| 2005/0050953 A1 | * | 3/2005 | Yamada et al. | 73/204.26 |
| 2005/0066707 A1 | * | 3/2005 | Katsuki et al. | 73/23.21 |
| 2005/0186696 A1 | * | 8/2005 | Yamada et al. | 438/48 |

FOREIGN PATENT DOCUMENTS

JP   2000283814 A   * 10/2000
JP   2003-130834   5/2003

* cited by examiner

Primary Examiner—Carol S. W. Tsai
(74) Attorney, Agent, or Firm—Harness, Dickey & Pierce, PLC (57) ABSTRACT

The method of detecting the hydrogen concentration by using a first heat-generating resistor of which a first electrophysical quantity varies depending upon the hydrogen concentration and a second heat-generating resistor which is neighboring said first heat-generating resistor in a direction of gas flow and of which a second electrophysical quantity varies depending upon the hydrogen concentration as does the first electrophysical quantity, to detect the concentration of hydrogen based on the first electrophysical quantity and the second electrophysical quantity, the method comprising: calculating the amount of change in a target physical quantity, which is either the first electrophysical quantity or the second electrophysical quantity, calculating the correction amount based on a difference between the first electrophysical quantity and the second electrophysical quantity, and a calculating the concentration of hydrogen based on a difference between the amount of change in the target physical quantity and the correction amount.

20 Claims, 8 Drawing Sheets

Fig.8

DEVICE FOR DETECTING HYDROGEN CONCENTRATION AND METHOD OF DETECTING HYDROGEN CONCENTRATION

FIELD OF THE INVENTION

The present invention relates to a device for detecting hydrogen concentration and a method of detecting hydrogen concentration.

BACKGROUND OF THE INVENTION

There has heretofore been known a device, for detecting hydrogen concentration, which utilizes the fact that the thermal conductivity of hydrogen is higher than that of the air.

For example, a hydrogen concentration detecting device disclosed in JP-A-2003-130834 detects hydrogen concentration based on a difference in the change of resistance between a detector element and a reference element both of which containing a thermistor therein.

According to the hydrogen concentration detecting device disclosed in JP-A-2003-130834, however, a flow of gas such as the air or hydrogen around the detector element robs heat from the detector element causing a variation in the resistance thereof. Therefore, the value that is detected tends to be higher than the real hydrogen concentration.

SUMMARY OF THE INVENTION

It is, therefore, an object of the present invention to provide a device, for detecting hydrogen concentration, which provides high precision detection and a method thereof.

According to the invention described in claims 1 to 20, first and second electrophysical quantities, in first and second heat-generating resistors that vary depending upon the hydrogen concentration, also undergo a variation depending upon the flow of gas around the first and second heat-generating resistors. Therefore, the amounts of change in the first and second electrophysical quantities often include a component of change due to the hydrogen concentration and a component of change due to the gas flow. The first and second heat-generating resistors neighbor each other in the direction of gas flow and, the first and second electrophysical quantities similarly vary depending upon the hydrogen concentration. Therefore, there is almost no difference in the component of change due to the hydrogen concentration between the first electrophysical quantity and the second electrophysical quantity, but a difference occurs in the component of change due to the gas flow. Therefore, of the amount of change in the electrophysical quantities, the component of change due to the gas flow can be found based on a difference between the first electrophysical quantity and the second electrophysical quantity.

Owing to the above-mentioned principle, and according to the invention described in claims 1–20, the component of change due to the gas flow in the amount of change in the target physical quantity which is one of either the first electrophysical quantity or the second electrophysical quantity, is calculated as a correction amount based on a difference between the first electrophysical quantity and the second electrophysical quantity. A difference between the correction amount and the amount of change in the target physical quantity, substantially represents a component of change due to the hydrogen concentration. Therefore, the hydrogen concentration can be precisely calculated based on the above difference. According to the invention described in claims 1–20, it is possible to increase the precision for detecting the hydrogen concentration.

The first electrophysical quantity and the second electrohysical quantity may be power consumption values as in, for example, the invention described in claims 2 and 12, or may be resistances as in the invention described in claims 3 and 13.

According to the invention described in claims 4 and 14, a deviation between the target physical quantity at a reference timing when the hydrogen concentration and the gas flow become substantially 0 around the first and second heat-generating resistors and the target physical quantity at the time of detecting the concentration, is regarded to be the amount of change in the target physical quantity. Therefore, the zero point in the amount of change represents the target physical quantity at the reference timing. The target physical quantity at the reference timing can be precisely known in advance, such as before the shipment of the device equipped with the first and second heat-generating resistors. Therefore, the amount of change in the target physical quantity can be precisely found from the target physical quantity, at the reference timing, as the zero point.

The first and second electrophysical quantities vary depending upon the temperature around the first and second heat-generating resistors (hereinafter simply referred to as an ambient temperature).

According to the invention described in claims 5 and 15, therefore, the target physical quantity at the reference timing is varied based upon the ambient temperature. Therefore, an error due to a change in the ambient temperature hardly occurs in the amount of change in the target physical quantity with the target physical quantity at the reference timing as the zero point. According to the invention described in claims 6 and 16, further, the amount of correcting the hydrogen concentration is calculated based on the difference between the first electrophysical quantity and the second electrophysical quantity and on the ambient temperature. Therefore, the correction amount that is calculated seldom contains an error caused by a change in the ambient temperature. According to the invention described in claims 7 and 17, the hydrogen concentration is calculated based on a difference between the amount of change in the target physical quantity and the correction amount, and upon the ambient temperature. Therefore, the hydrogen concentration that is calculated seldom contains an error caused by a change in the ambient temperature.

According to the invention described in claims 8 and 18, the ambient temperature is detected based on the resistance that varies in the temperature-detecting resistor. Here, the temperature-detecting resistor neighbors either the first heat-generating resistor or the second heat-generating resistor, and a correct ambient temperature can be found from the resistance of the temperature-detecting resistor.

According to the invention described in claims 9 and 19, the first and second heat-generating resistors have straight portions perpendicular to the axes of the directions of gas flow. Therefore, the first and second electrophysical quantities vary sharply depending upon the gas flow, and improved sensitivity to the gas flow is obtained.

According to the invention described in claims 10 and 20, the first and second heat-generating resistors are contained in a membrane to prevent the occurrence of a difference between the first electrophysical quantity and the second electrophysical quantity caused by factors other than the gas flow.

DESCRIPTION OF THE PREFERRED EMBODIMENT

An embodiment of the invention will now be described with reference to the drawings.

Figure 2:
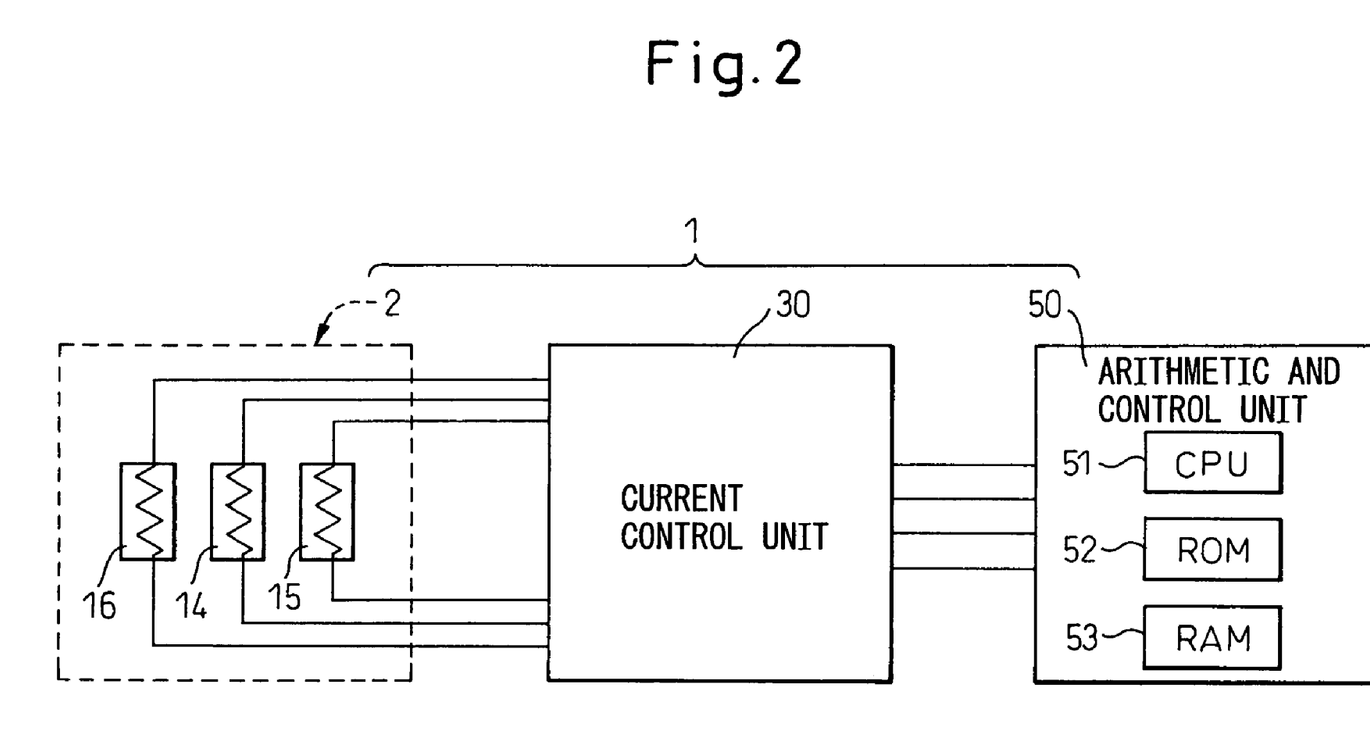
FIG. 2 is a block diagram illustrating the constitution of the device for detecting hydrogen concentration according to the embodiment of the present invention.

FIG. 2 illustrates a device for detecting hydrogen concentration according to an embodiment of the invention. The device 1 for detecting hydrogen concentration is installed in an engine compartment or a passenger compartment of an automobile that uses hydrogen as a fuel, and detects the concentration of hydrogen leaking into the compartment. The device 1 for detecting hydrogen concentration includes a sensing unit 2, a current control unit 30 and an arithmetic and control unit 50.

Figure 3:
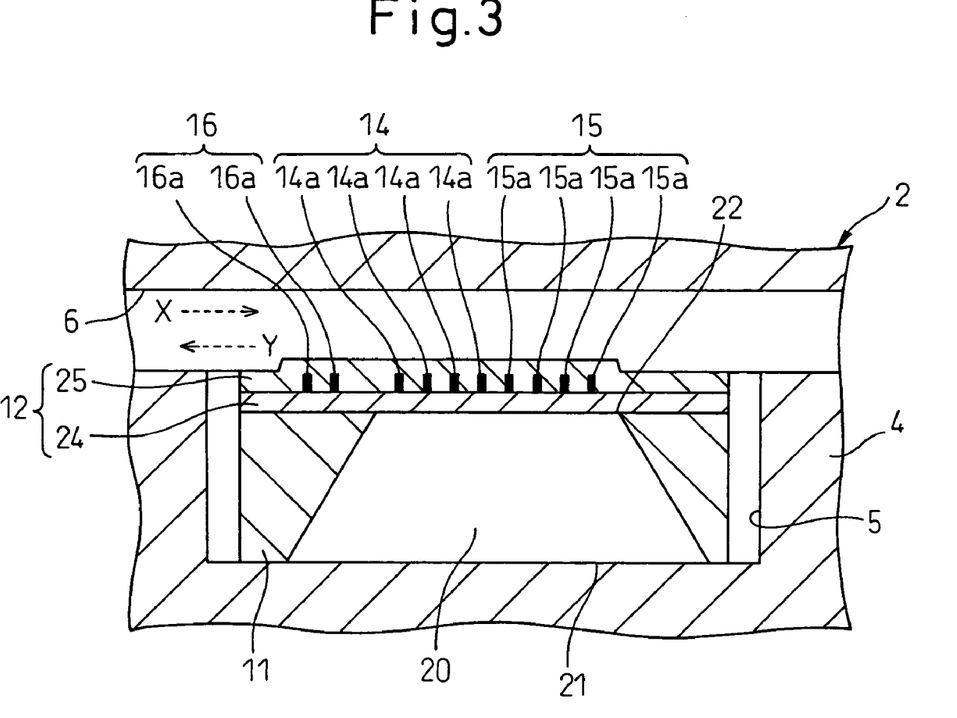
FIG. 3 is a longitudinal sectional view illustrating a sensing unit according to the embodiment of the present invention.
Figure 4:
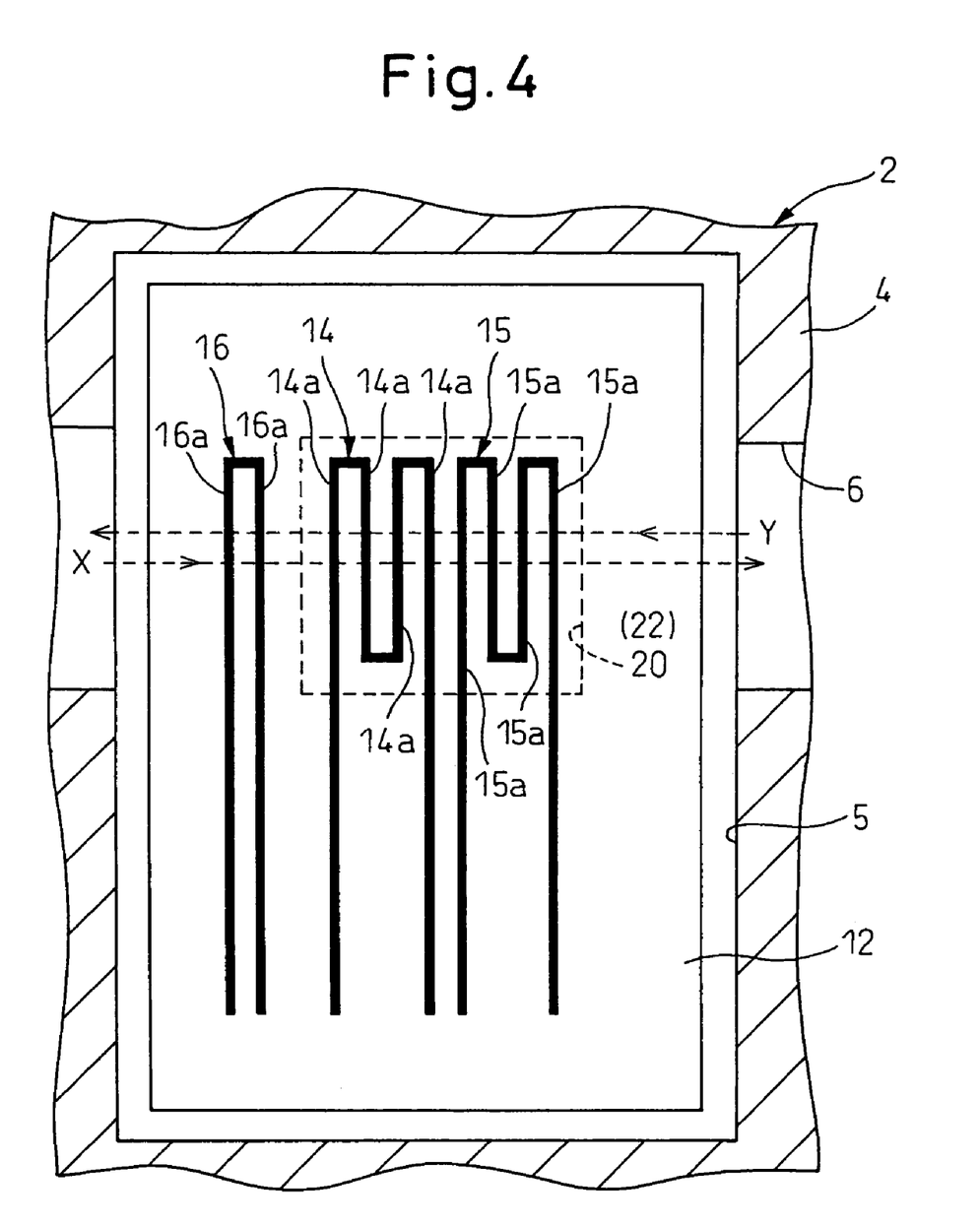
FIG. 4 is a transverse sectional view illustrating the sensing unit according to the embodiment of the present invention.

Referring to FIGS. 3 and 4, the sensing unit 2 is constituted by a housing 4, a base body 11, a membrane 12, heat-generating resistors 14 and 15, and a temperature-detecting resistor 16.

The housing 4 includes a recessed accommodating portion 5 for accommodating and securing the base body 11, and a flow path 6 for discharging the gas after the gas is introduced onto the membrane 12 from the compartment.

The base body 11 is made of single-crystal silicon in the shape of nearly a flat plate. The base body 11 has a cavity 20 penetrating in the direction of the thickness of the plate. The cavity 20 has its one opening 21 closed by the bottom wall of the recessed accommodating portion 5 of the housing 4 thereby to constitute a recessed portion. The other opening 22 of the cavity 20 is covered with the membrane 12 of the form of a thin film. The gas introduced into the housing 4 through the flow path 6 flows through the flow path 6 of the membrane 12 on the side opposite to the base body 11. In FIGS. 3 and 4, the arrow X represents the forward direction of gas flow and the arrow Y represents the reverse direction of gas flow.

The membrane 12 is constituted by a silicon oxide film 24 and a silicon nitride film 25 laminated by a micro-machine technology. The membrane 12 on the side of the silicon oxide film 24 is secured to the outer peripheral side of the opening 22 of the base body 11. The membrane 12 contains therein the heat-generating resistors 14 and 15 and holds them between the silicon oxide film 24 and the silicon nitride film 25 on the opening 22. Therefore, the membrane 12 works as a heat-insulating member for insulating the heat between the heat-generating resistors 14 and 15 and, further, it works as a protection film for protecting the heat-generating resistors 14 and 15. The membrane 12 further contains therein the temperature-detecting resistor 16 and holds it between the silicon oxide film 24 and the silicon nitride film 25.

The heat-generating resistors 14, 15 and the temperature-detecting resistor 16 are formed by patterning a metal film such as a Pt film or a similar film. The temperature-detecting resistor 16, the heat-generating resistor 14 and the heat-generating resistor 15 are arranged in this order along the forward direction X of gas flow. In the both directions X and Y of gas flow, therefore, the temperature detecting resistor 16 and the heat-generating resistor 14 neighbor each other, and the heat-generating resistor 14 and the heat-generating resistor 15 neighbor each other. The heat-generating resistors 14 and 15, having the same specifications, assume a meandering shape each being bent at six places, and each forming four straight portions 14a and 15a perpendicular to the axes of the both directions X and Y of gas flow. Gaps between the four straight portions 14a, gaps between the four straight portions 15a, and gaps between the neighboring straight portions 14a, 15a (i.e., gaps between the heat-generating resistors 14 and 15) are set to be, for example, not larger than 1 mm. The temperature-detecting resistor 16 has a U-shape, is bent at two places, and forms two straight portions 16a perpendicular to the axes of the both directions X and Y of gas flow. The gap between the two straight portions 16a and the gap between the neighboring straight portions 16a and 14a (i.e., the gap between the temperature-detecting resistor 16 and the heat-generating resistor 14) are set to be, for example, not larger than 1 mm.

The current control unit 30 shown in FIG. 2 is constituted by an electric circuit, and is electrically connected to the heat-generating resistors 14, 15 and to the temperature-detecting resistor 16. The current control unit 30 supplies electric currents to the heat-generating resistors 14, 15 and to the temperature-detecting resistor 16 in a controlled manner.

Concretely speaking, the current control unit 30 carries out a feedback control operation while maintaining the resistances of the resistors 14 and 15 constant so that the heat-generating temperatures of the heat-generating resistors 14 and 15 become constant. In this case, the current control unit 30 of this embodiment works so that the resistances of the heat-generating resistors 14 and 15 become equal to each other, and that the power consumption values $W_1$ and $W_2$ of the heat-generating resistors 14 and 15 similarly vary depending upon the hydrogen concentration around the resistors. Therefore, a correlation becomes in agreement between the power consumption values $W_1$, $W_2$ and the hydrogen concentration when the gas flow becomes substantially 0 around the heat-generating resistors 14 and 15.

As a result of feedback control by the current control unit 30, the power consumption values $W_1$, $W_2$ of the heat-generating resistors 14 and 15 vary as described below.

When the hydrogen concentration and the gas flow become substantially zero around the heat-generating resistors 14 and 15, the power consumption values $W_1$ and $W_2$ of the heat-generating resistors 14 and 15 assume nearly the same reference value $W_B$.

Figure 5A:
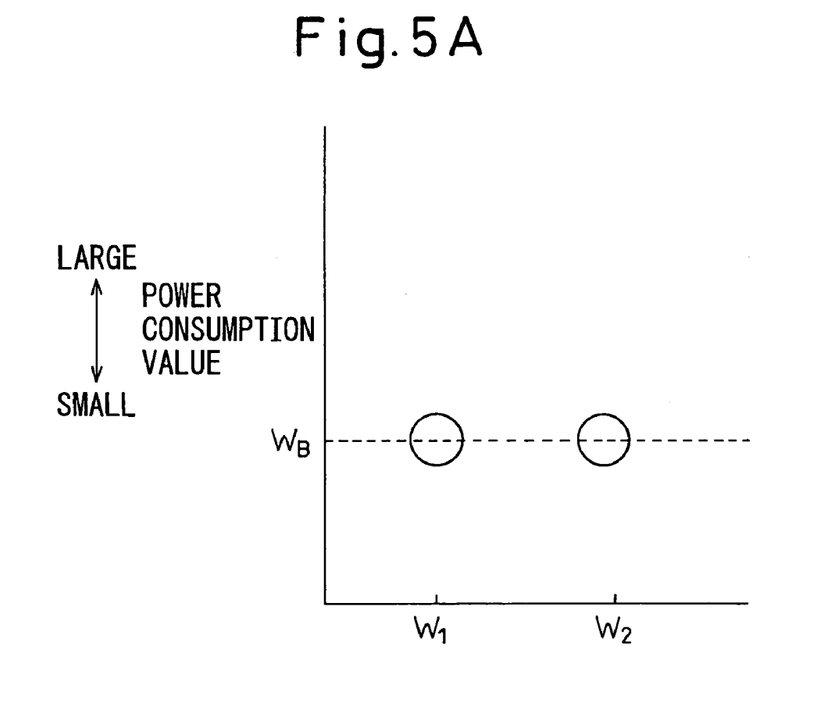
FIGS. 5A and 5B are graphs illustrating the operation of the device for detecting hydrogen concentration according the embodiment of the present invention.
Figure 5B:
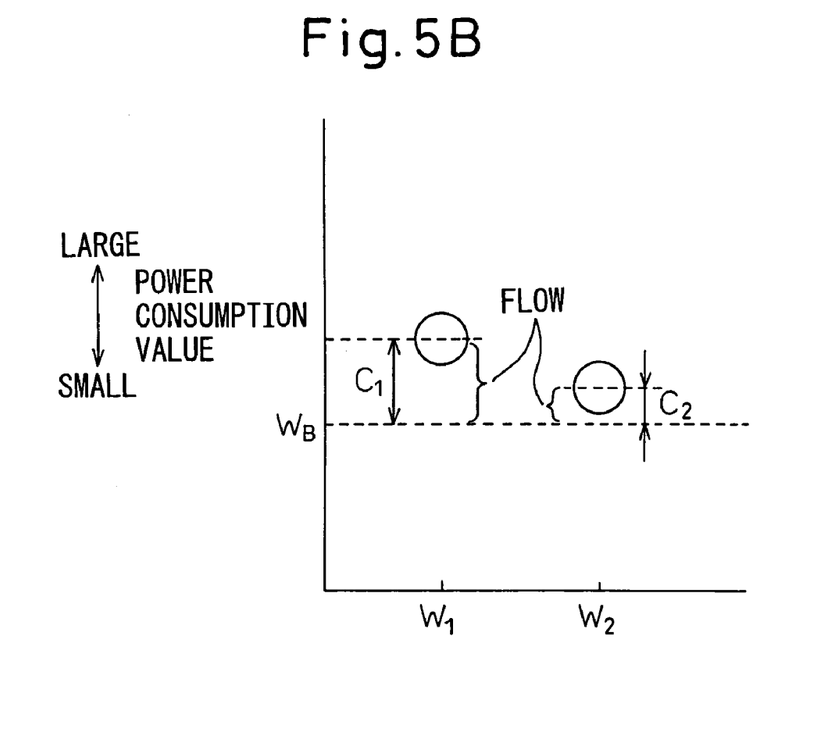

When the hydrogen concentration becomes substantially zero but the gas flows around the heat-generating resistors 14 and 15, the power consumption values $W_1$ and $W_2$ of the heat-generating resistors 14 and 15 become greater than the reference value $W_B$ and different from each other as shown in FIG. 5B. When the gas is flowing in the forward direction X, in this case, the power consumption value $W_1$ of the heat-generating resistor 14 on the upstream side becomes greater than the power consumption value $W_2$ of the heat-generating resistor 15 on the downstream side. When the gas is flowing in the reverse direction Y, on the other hand, the power consumption value $W_2$ of the heat-generating resistor 15 on the upstream side becomes greater than the power consumption value $W_1$ of the heat-generating resistor 14 on the downstream side. In either case, the amounts $C_1$ and $C_2$ of change in the power consumption values $W_1$ and $W_2$ represented by deviations of the power consumption values $W_1$ and $W_2$ of the heat-generating resistors 14 and 15 from the reference value $W_B$, are solely components of change due to the gas flow.

Figure 6A:
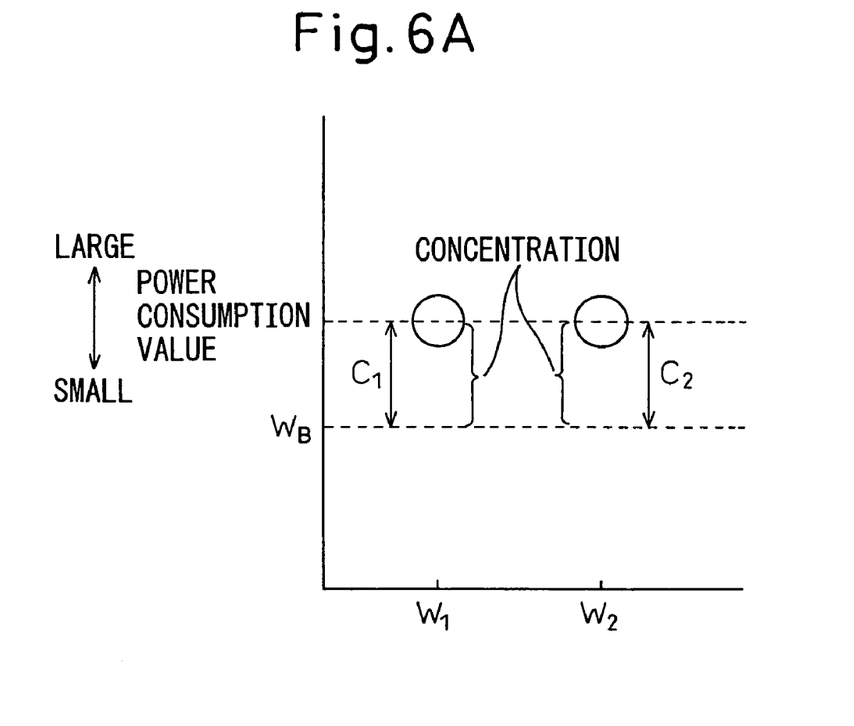
FIGS. 6A and 6B are graphs illustrating the operation of the device for detecting hydrogen concentration according the embodiment of the present invention.

When the hydrogen concentration becomes greater than zero but the gas flow becomes substantially zero around the heat-generating resistors 14 and 15, the power consumption values $W_1$ and $W_2$ of the heat-generating resistors 14 and 15 become greater than the reference value WB and become nearly equal to each other as shown in FIG. 6A. Here, the amounts $C_1$ and $C_2$ of change in the power consumption values $W_1$ and $W_2$ of the heat-generating resistors 14 and 15 are solely components of change due to the hydrogen concentration.

Figure 6B:
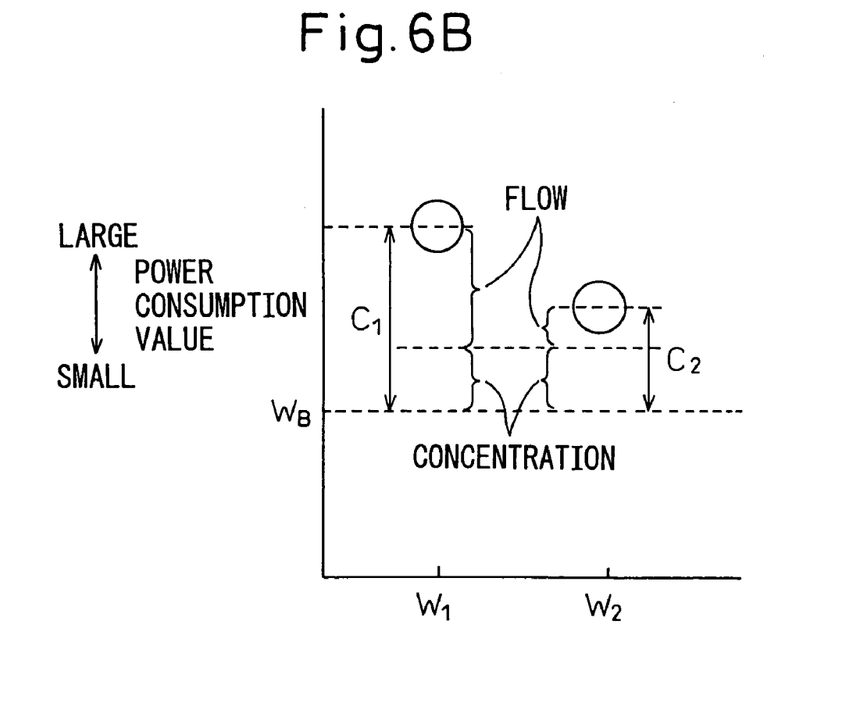

When the hydrogen concentration becomes greater than zero and the gas flows around the heat-generating resistors 14 and 15 as shown in FIG. 6B, the power consumption values $W_1$ and $W_2$, of the heat-generating resistors 14 and 15, become greater than the reference value $W_B$ and become different from each other. Here, when the gas is flowing in the forward direction X as shown in FIG. 6B, the power consumption value $W_1$ of the heat-generating resistor 14 on the upstream side becomes greater than the power consumption value $W_2$ of the heat-generating resistor 15 on the downstream side. When the gas is flowing in the reverse direction Y, on the other hand, the power consumption value $W_2$ of the heat-generating resistor 15 on the upstream side becomes greater than the power consumption value $W_1$ of the heat-generating resistor 14 of the downstream side. In either case, the amounts $C_1$ and $C_2$ of change in the power consumption values $W_1$ and $W_2$ of the heat-generating resistors 14 and 15 become the amounts obtained by adding the components of change due to the gas flow to the components of change due to the hydrogen concentration. Here, the amounts $C_1$ and $C_2$ of change in the power consumption values $W_1$ and $W_2$ are different from each other, as shown in FIG. 6B, because there is a difference in the components of change, due to the gas flow, even though there is no difference in the components of change due to the hydrogen concentration.

When an instruction signal is received from the arithmetic and control unit 50, further, the current control unit 30 supplies a predetermined voltage or a predetermined current to the temperature-detecting resistor 16. Therefore, the resistance R of the temperature-detecting resistor 16 varies depending upon the temperature T around the temperature-detecting resistor 16. In this embodiment, the temperature-detecting resistor 16 is located close to the heat-generating resistors 14 and 15. Therefore, the ambient temperature T of the temperature-detecting resistor 16 is substantially in agreement with the ambient temperature of the heat-generating resistors 14 and 15.

Referring to FIG. 2, the arithmetic and control unit 50 which is the "concentration detector means" is constituted chiefly by a microcomputer having a CPU 51, a ROM 52 and a RAM 53. The arithmetic and control unit 50 is electrically connected to the current control unit 30, and receives, from the current control unit 30, the signals representing the power consumption values $W_1$ and $W_2$ of the heat-generating resistors 14 and 15, and the resistance R of the temperature-detecting resistor 16. The arithmetic and control unit 50 has the CPU 51 execute a detection program, stored in the ROM 52, to detect the ambient temperature T based on the resistance R and to detect the hydrogen concentration based on the ambient temperature T and on the power consumption values $W_1$, $W_2$. At this moment, the power consumption values $W_1$, $W_2$ and the ambient temperature T are stored in the RAM 53.

Figure 1:
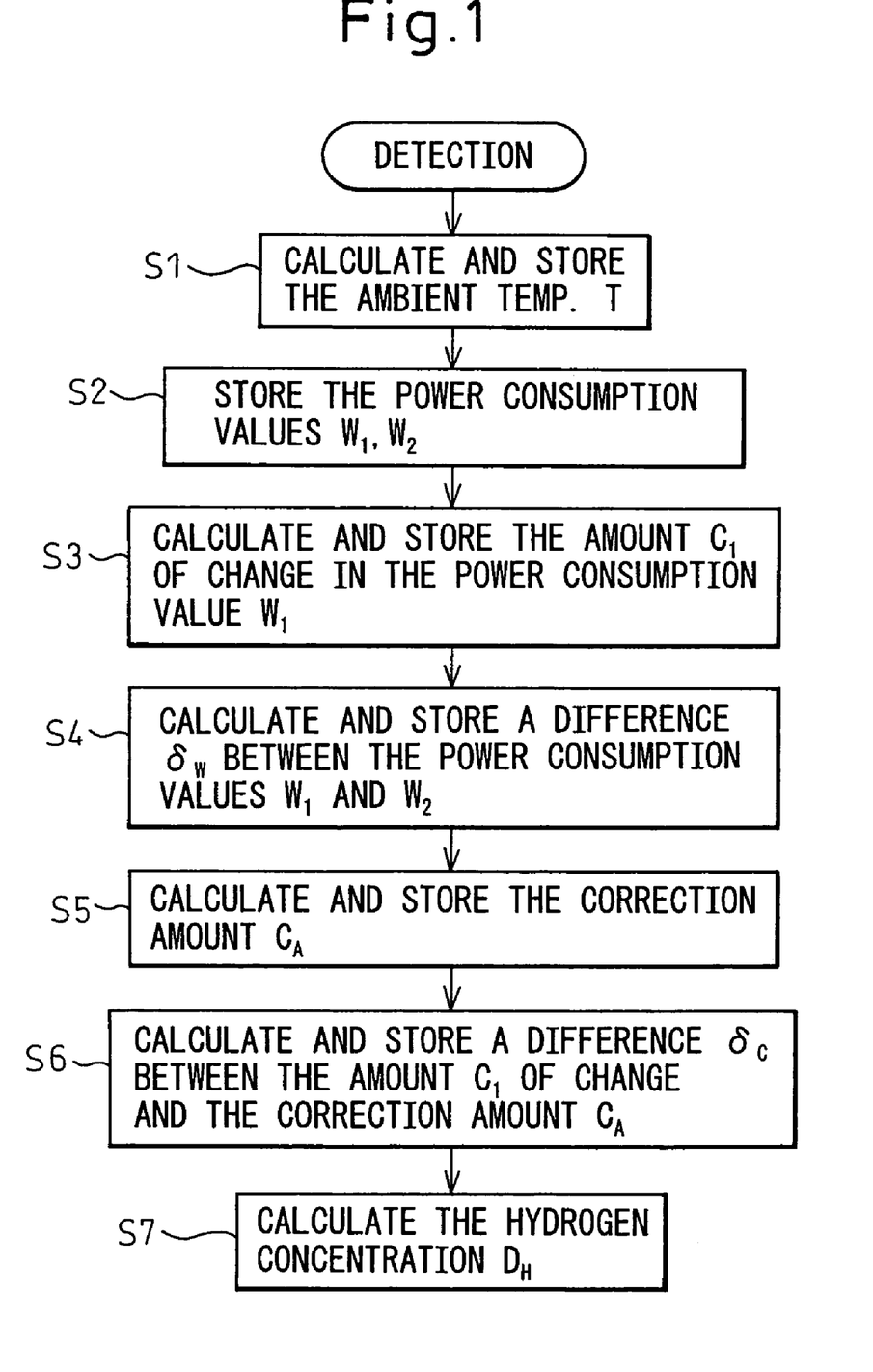
FIG. 1 is a flowchart illustrating the operation of a device for detecting hydrogen concentration according to an embodiment of the present invention.

The steps successively executed by the arithmetic and control unit 50, as the detection program is executed by the CPU 51, will now be described in detail according to the flowchart of FIG. 1.

At step S1, first, an instruction signal is given to the current control unit 30 to supply a current to the temperature-detecting resistor 16 and, then, a signal representing the resistance R is received from the current control unit 30. At step S1, further, an ambient temperature T is calculated based on the resistance R represented by the received signal, and is stored in the RAM 53. The "temperature detecting means" is represented by a portion of the arithmetic and control unit 50 that executes the above step S1, by the temperature-detecting resistor 16 and by the current control unit 30, and the "temperature detecting step" is represented by the above step S1.

At step S2, an instruction signal is given to the current control unit 30, whereby signals representing the power consumption values $W_1$ and $W_2$ are received from the current control unit 30, and the power consumption values $W_1$ and $W_2$ represented by the received signals are stored in the RAM 53.

At step S3, attention is given to the one power consumption value $W_1$ to calculate a deviation between the power consumption value $W_1$ and the reference value $W_B$, i.e., to calculate the amount $C_1$ of change in the power consumption value $W_1$. In this embodiment, at this moment, the reference value WB is varied depending upon the ambient temperature T. The relationship between the reference value WB and the ambient temperature T has been measured in advance prior to the shipment of the device 1, and has been stored in the ROM 52 in the form of a map of a function. At step S3, further, the amount $C_1$ of change that is calculated is stored in the RAM 53. The "amount-of-change calculation means" is represented by a portion of the arithmetic and control unit 50 that executes the above step S3, and the "amount-of-change calculation step" is represented by the above step S3.

At step S4, a difference $\delta_W$, between the power consumption values $W_1$ and $W_2$, is calculated and is stored in the RAM 53.

At step S5, of the amount $C_1$ of change in the power consumption value $W_1$, the component of change due to the gas flow is estimated as the correction amount $C_A$ based on the difference $\delta_W$ between the power consumption values $W_1$ and $W_2$. In this embodiment, in this case, the correction amount $C_A$ is so calculated as to be proportional to the difference $\delta_W$, and the coefficient of proportion is varied depending upon the ambient temperature T. A correlation among the difference $\delta_W$, the ambient temperature T and the correction amount $C_A$ has been stored in advance in the ROM 52 in the form of a map or a function. At step S5, further, the calculated correction amount $C_A$ is stored in the RAM 53. The "correction amount calculation means" is represented by a portion of the arithmetic and control unit 50 which executes the step S5, and the "correction amount calculation step" is represented by the step S5.

At step S6, a difference $\delta_C$ between the amount $C_1$ of change in the power consumption value $W_1$ and the correction amount $C_A$ is calculated and is stored in the RAM 53.

At step S7, the hydrogen concentration DH is calculated based on the difference $\delta_C$ between the amount $C_1$ of change in the power consumption value $W_1$ and the correction amount $C_A$. In this embodiment, in this case, the correction amount $D_H$ is so calculated as to be proportional to the difference $\delta_C$, and the coefficient of proportion is varied depending upon the ambient temperature T. A correlation among the difference $\delta_C$, the ambient temperature T and the calculated hydrogen concentration $D_H$ has been stored in advance in the ROM 52 in the form of a map or a function. The "concentration calculation means" is represented by a portion of the arithmetic and control unit 50 which executes the step S7, and the "concentration calculation step" is represented by the step S7.

In this embodiment, which detects the hydrogen concentration as described above, the values $C_1$, $C_A$, $\delta_C$ and $D_H$ calculated at steps S3, S5, S6 and S7 undergo changes as described above.

When the hydrogen concentration and the gas flow are substantially 0 around the heat-generating resistors 14 and 15, the amount of change $C_1$ in the power consumption value $W_1$ and the correction amount $C_A$ become 0, and the difference $\delta_C$ between $C_1$ and $C_A$ becomes 0, too. Therefore, the hydrogen concentration $D_H$ which varies in proportion to the difference $\delta_C$ becomes 0.

When the hydrogen concentration becomes substantially 0 but the gas flows around the heat-generating resistors 14 and 15, the amount $C_1$ of change in the power consumption value $W_1$ becomes solely the component of change due to the gas flow, and becomes in agreement with the correction amount $C_A$, whereby the difference $\delta_C$ between $C_1$ and $C_A$ becomes 0. Therefore, the hydrogen concentration $D_H$ that varies in proportion to the difference $\delta_C$ becomes 0.

When the hydrogen concentration becomes greater than 0 while the gas flow is substantially 0 around the heat-generating resistors 14 and 15, the amount $C_1$ of change in the power consumption value $W_1$ is solely the component of change in the hydrogen concentration while the correction amount $C_A$ is 0. Therefore, the difference $\delta_C$ between $C_1$ and $C_A$ becomes in agreement with the component of change due to the hydrogen concentration. Accordingly, the hydrogen concentration $D_H$ which varies in proportion to the difference $\delta_C$ precisely represents the real concentration.

When the hydrogen concentration is greater than 0 and the gas flows around the heat-generating resistors 14 and 15, the amount $C_1$ of change in the power consumption value $W_1$ becomes the sum of the component of change due to the hydrogen concentration and the component of change due to the gas flow. Accordingly, the difference $\delta_C$ between the amount $C_1$ of change and the correction amount $C_A$ becomes equal to the amount $C_1$ of change from which the component of change due to the gas flow is subtracted, and becomes in agreement with the component of change due to the hydrogen concentration. Therefore, the hydrogen concentration $D_H$ which varies in proportion to the difference $\delta_C$ precisely represents the real concentration.

In this embodiment as described above, even when the gas flows around the heat-generating resistors 14 and 15, the detected hydrogen concentration $D_H$ is not affected by the gas flow.

At steps S3, S5 and S7, further, the values $C_1$, $C_A$ and $D_H$ are calculated by taking the ambient temperature T into consideration; i.e., the values $C_1$, $C_A$ and $D_H$ are avoided from containing errors that stem from changes in the ambient temperature T. Therefore, the detected the hydrogen concentration $D_H$ is not affected by a change in the ambient temperature T.

Further, the heat-generating resistors 14 and 15 have straight portions 14a and 15a perpendicular to the axes of the directions X, Y of gas flow. Therefore, the power consumption values $W_1$ and $W_2$ of the resistors 14 and 15 sensitively vary in response to the gas flow. At step S5, therefore, the correction amount $C_A$ can be precisely obtained as a component of change due to the gas flow, making it possible to detect the hydrogen concentration DH which is hardly affected by the gas flow.

Further, the membrane 12 has the function of insulating the heat between the heat-generating resistors 14 and 15 and for protecting the resistors 14 and 15, preventing the occurrence of difference between the power consumption values $W_1$ and $W_2$ of the heat-generating resistors 14, 15 due to factors other than the gas flow, such as mutual thermal action and shocks between the resistors 14 and 15. Therefore, there is detected the hydrogen concentration $D_H$ which is not affected by the mutual thermal action or shocks between the resistors 14 and 15.

According to this embodiment as described above, the hydrogen concentration is detected highly precisely.

In the above-mentioned embodiment, the resistances of the heat-generating resistors 14 and 15 are maintained constant and equal to each other, and the hydrogen concentration is detected based on the power consumption values $W_1$ and $W_2$ of the heat-generating resistors 14 and 15. It is, however, also possible to maintain the power consumption values $W_1$ and $W_2$ of the heat-generating resistors 14 and 15 constant and equal to each other, and to detect the hydrogen concentration based on the resistances of the heat-generating resistors 14 and 15.

In the above embodiment, further, the heat-generating resistors 14 and 15 and the temperature-detecting resistor 16 are formed of a metal film such as a Pt film. These resistors 14, 15 and 16, however, may be formed of a semiconductor film such as a polysilicon film.

According to the above embodiment, the temperature-detecting resistor 16 is provided neighboring the heat-generating resistor 14. However, the temperature-detecting resistor 16 may be provided neighboring the heat-generating resistor 15.

In the above embodiment, further, the ambient temperature T is detected by the temperature-detecting resistor 16. However, the ambient temperature T may be detected by using any other widely-known temperature sensor.

At steps S3, S5 and S7 of the above embodiment, further, the values $C_1$, $C_A$ and $D_H$ are calculated by taking the ambient temperature T into consideration. However, at least any one of the values $C_1$, $C_A$ and $D_H$ may be calculated irrespective of the ambient temperature T. When the values $C_1$, $C_A$ and $D_H$ are to be all calculated irrespective of the ambient temperature T, there is no need to provide the temperature-detecting resistor 16 or the temperature sensor in its place.

Figure 7A:
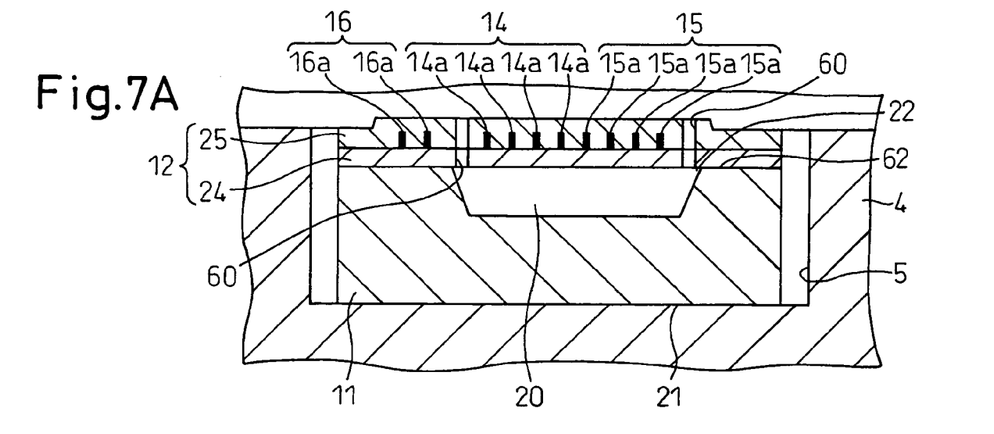
FIG. 7A is a longitudinal sectional view illustrating the sensing unit according to a modified example of the first embodiment of the invention.
Figure 7B:
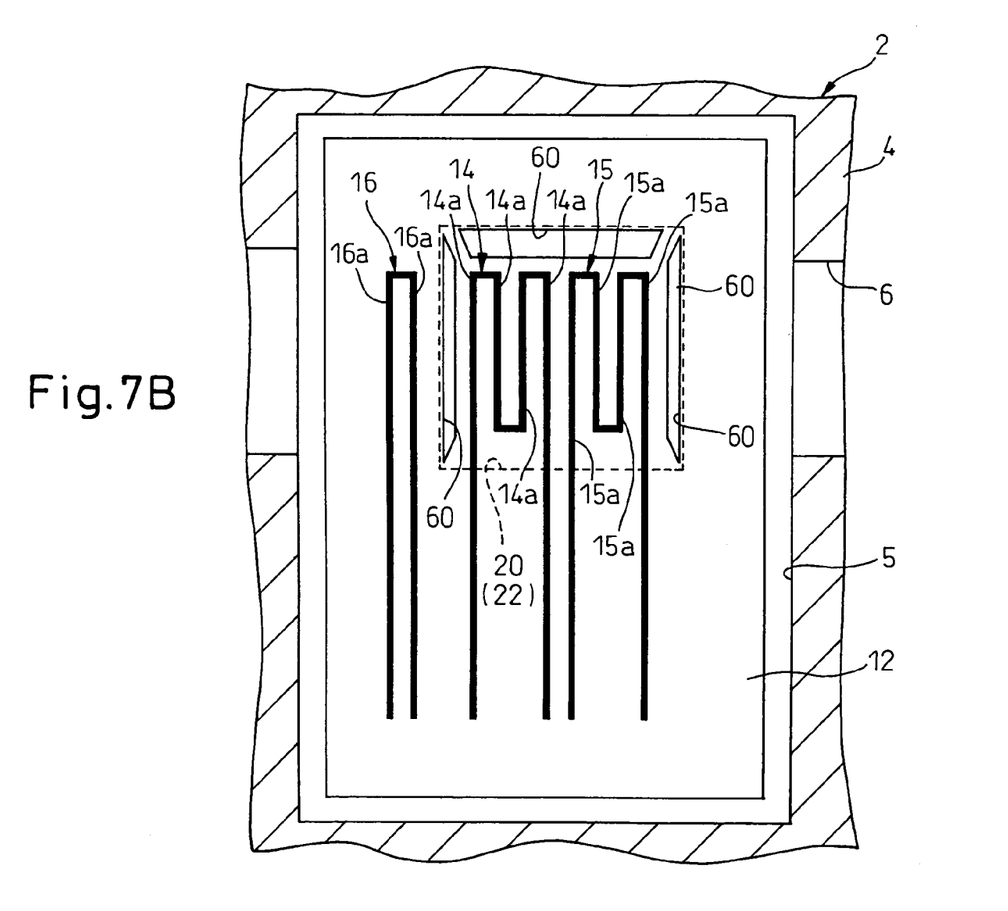
FIG. 7B is a transverse sectional view illustrating the sensing unit according to the modified example of the first embodiment of the invention.
Figure 8:
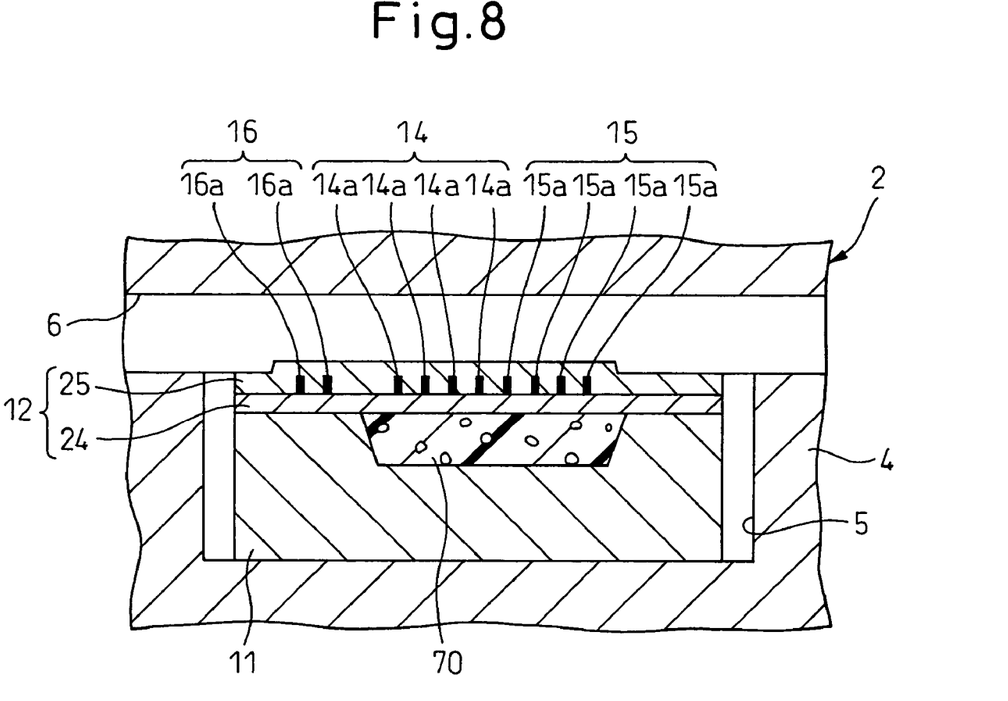
FIG. 8 is a longitudinal sectional view illustrating the sensing unit according to another modified example of the first embodiment of the invention.

Further, according to a modified example of the above embodiment as illustrated in FIG. 7, the cavity 20 may be formed in the substrate 11 from the side of the front surface 62 of the flow path 6 by using a chemical that acts upon the substrate 11 without the cavity 20 by passing the chemical through at least one window 60 perforated in a portion of the membrane 12 surrounding the heat-generating resistors 14 and 15 in the direction of thickness. Here, as shown in FIG. 7, the cavity 20 may be formed to open on only the side of the front surface 62 without penetrating through the substrate 11. According to another modified example shown in FIG. 8, further, a porous portion 70 may be formed instead of the cavity 20 by, for example, using a chemical that acts upon the substrate 11.

At step S3 of the above embodiment, further, a deviation between the power consumption value $W_1$ and the reference value WB is calculated as the amount $C_1$ of change in the power consumption value $W_1$ by detecting the power consumption value $W_1$ of the heat-generating resistor 14. At step S3, however, it is also possible to calculate a deviation between the power consumption value $W_2$ and the reference value $W_B$ as the amount $C_2$ of change in the power consumption value $W_2$ by detecting the power consumption value $W_2$ of the heat-generating resistor 15. In this case, at step S5, of the amount $C_2$ of change in the power consumption value $W_2$, a component of change due to the gas flow is estimated based on a difference $\delta_W$ between the power consumption values $W_1$ and $W_2$ and is regarded as the correction amount $C_A$ to calculate, at step S6, a difference $\delta_C$ between the amount $C_2$ of change in the power consumption value $W_2$ and the correction amount $C_A$. The above embodiment has dealt with a case where the present invention was applied to the device 1 for detecting the concentration of hydrogen leaking in the engine room or in the compartment of an automobile which uses hydrogen as a fuel. It is, however, also possible to apply the present invention to a device for detecting hydrogen concentration which detects the concentration of hydrogen fed to a fuel cell in the automobile that uses hydrogen as a fuel. Or, the invention may be applied to the device for detecting hydrogen-concentration which detects the concentration of hydrogen emitted to the exterior from the automobile that uses hydrogen as a fuel. Or, the invention may be applied to the device for detecting hydrogen concentration at a place other than an automobile that uses hydrogen as a fuel.

The invention claimed is:

1. A device for detecting hydrogen concentration comprising:
    a first heat-generating resistor of which a first electrophysical quantity varies depending upon the hydrogen concentration;
    a second heat-generating resistor neighboring said first heat-generating resistor in a direction of the gas flow and of which a second electrophysical quantity varies depending upon the hydrogen concentration as does said first electrophysical quantity; and
    concentration detector means for detecting the concentration of hydrogen based on said first electrophysical quantity and said second electrophysical quantity;
    wherein said concentration detector means includes:
    amount-of-change calculation means for calculating the amount of change in a target physical quantity, which is either said first electrophysical quantity or said second electrophysical quantity;
    correction amount calculation means for calculating the correction amount based on a difference between said first electrophysical quantity and said second electrophysical quantity; and
    concentration calculation means for calculating the concentration of hydrogen based on a difference between said amount of change and said correction amount.

2. A device for detecting hydrogen concentration according to claim 1, wherein said first electrophysical quantity and said second electrophysical quantity are power consumption values.

3. A device for detecting hydrogen concentration according to claim 1, wherein said first electrophysical quantity and said second electrophysical quantity are resistances.

4. A device for detecting hydrogen concentration according to claim 1, wherein said amount-of-change calculation means regards, as said amount of change, a deviation between said target physical quantity, at a reference timing at which the hydrogen concentration and the gas flow become substantially zero around said first heat-generating resistor and said second heat-generating resistor, and said target physical quantity at the time of detecting the concentration.

5. A device for detecting hydrogen concentration according to claim 4, further comprising temperature-detecting means for detecting an ambient temperature around said first heat-generating resistor and said second heat-generating resistor,
    wherein said amount-of-change calculation means varies said target physical quantity at said reference timing depending upon said ambient temperature.

6. A device for detecting hydrogen concentration according to claim 1, further comprising temperature-detecting means for detecting an ambient temperature around said first heat-generating resistor and said second heat-generating resistor,
    wherein said correction amount calculation means calculates said correction amount based upon a difference between said first electrophysical quantity and said second electrophysical quantity, and upon said ambient temperature.

7. A device for detecting hydrogen concentration according to claim 1, further comprising temperature-detecting means for detecting an ambient temperature around said first heat-generating resistor and said second heat-generating resistor,
    wherein said concentration calculation means calculates the concentration of hydrogen based upon a difference between said amount of change and said correction amount, and upon said ambient temperature.

8. A device for detecting hydrogen concentration according to claim 5, wherein said temperature-detecting means has a temperature-detecting resistor that is neighboring either said first heat-generating resistor or said second heat-generating resistor, and detects said ambient temperature based on a resistance that varies in said temperature-detecting resistor.

9. A device for detecting hydrogen concentration according to claim 1, wherein each of said first heat-generating resistor and said second heat-generating resistor has a straight portion perpendicular to the axes of the directions of gas flow.

10. A device for detecting hydrogen concentration according to claim 1, further comprising a membrane containing said first heat-generating resistor and said second heat-generating resistor therein.

11. A method of detecting hydrogen concentration by using a first heat-generating resistor of which a first electrophysical quantity varies depending upon the hydrogen concentration and a second heat-generating resistor which is neighboring said first heat-generating resistor in a direction of gas flow and of which a second electrophysical quantity varies depending upon the hydrogen concentration as does said first electrophysical quantity, to detect the concentration of hydrogen based on said first electrophysical quantity and said second electrophysical quantity, said method comprising the steps of:

calculating the amount of change in a target physical quantity, which is either said first electrophysical quantity or said second electrophysical quantity;

calculating the correction amount based on a difference between said first electrophysical quantity and said second electrophysical quantity; and calculating the concentration of hydrogen based on a difference between said amount of change and said correction amount.

12. A method of detecting hydrogen concentration according to claim 11, wherein said first electrophysical quantity and said second electrophysical quantity are power consumption values.

13. A method of detecting hydrogen concentration according to claim 11, wherein said first electrophysical quantity and said second electrophysical quantity are resistances.

14. A method of detecting hydrogen concentration according to claim 11, wherein said step of calculating the amount of change regards, as said amount of change, a deviation between said target physical quantity, at a reference timing at which the hydrogen concentration and the gas flow become substantially zero around said first heat-generating resistor and said second heat-generating resistor, and said target physical quantity at the time of detecting the concentration.

15. A method of detecting hydrogen concentration according to claim 14, further comprising a step of detecting an ambient temperature around said first heat-generating resistor and said second heat-generating resistor, wherein said step of calculating the amount of change varies said target physical quantity at said reference timing depending upon said ambient temperature.

16. A method of detecting hydrogen concentration according to claim 11, further comprising a step of detecting an ambient temperature around said first heat-generating resistor and said second heat-generating resistor, wherein said step of calculating the correction amount calculates said correction amount based upon a difference between said first electrophysical quantity and said second electrophysical quantity, and upon said ambient temperature.

17. A method of detecting hydrogen concentration according to claim 11, further comprising a step of detecting an ambient temperature around said first heat-generating resistor and said second heat-generating resistor, wherein said step of calculating the concentration calculates the concentration of hydrogen based upon a difference between said amount of change and said correction amount, and upon said ambient temperature.

18. A method of detecting hydrogen concentration according to claim 15, wherein said step of detecting the temperature uses a temperature-detecting resistor that is neighboring either said first heat-generating resistor or said second heat-generating resistor, and detects said ambient temperature based on a resistance that varies in said temperature-detecting resistor.

19. A method of detecting hydrogen concentration according to claim 11, wherein each of said first heat-generating resistor and said second heat-generating resistor has a straight portion perpendicular to the axes of the directions of gas flow.

20. A method of detecting hydrogen concentration according to claim 11, wherein said first heat-generating resistor and said second heat-generating resistor are contained in a membrane.

* * * * *